(12) United States Patent
Zhong et al.

(10) Patent No.: US 6,298,264 B1
(45) Date of Patent: Oct. 2, 2001

(54) APPARATUS AND METHOD FOR MACROMOLECULE DELIVERY INTO LIVING CELLS

(75) Inventors: Pei Zhong; Franklin H. Cocks, both of Durham; Glenn M. Preminger, Chapel Hill; Haifan Lin, Durham, all of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/144,381

(22) Filed: Aug. 31, 1998

(51) Int. Cl.$^7$ ............................................. A61N 1/30

(52) U.S. Cl. .............................. 604/20; 604/22

(58) Field of Search ................... 604/20, 21, 22; 601/2, 3, 4; 607/96, 97, 99, 100, 101; 600/439; 310/322, 334, 335

(56) References Cited

U.S. PATENT DOCUMENTS

| | | | |
|---|---|---|---|
| 4,664,111 | 5/1987 | Reichenberger et al. | 601/4 |
| 5,219,401 | 6/1993 | Cathignol | 600/439 |
| 5,403,590 | 4/1995 | Forse | 424/422 |
| 5,506,125 | 4/1996 | McCabe et al. | 435/172.1 |
| 5,582,578 | 12/1996 | Zhong et al. | 601/4 |
| 5,614,502 | 3/1997 | Flotte et al. | 514/34 |
| 5,658,892 | 8/1997 | Flotte et al. | 514/44 |
| 5,752,515 | 5/1998 | Jolesz et al. | 128/653.1 |
| 5,800,365 | 9/1998 | Zhong et al. | 601/4 |

OTHER PUBLICATIONS

M.T. Carnell, S.J. Barington, D.C. Emmony, "A Phase–Inverting Parabolic Concentrator for the Generation of Negative Waves in Water," Journal of Acoustical Society of America, 1997.

Pei Zhong, Iulian Cioanta, Songlin Zhu, Franklin H. Cocks, Glenn M. Preminger, "Effects of Tissue Constraint on Shock Wave–Induced Bubble Expansion In Vivo," Journal of Acoustic Society of America.

M. Delius, N. Weiss, S. Gambihler, A. Goetz, W. Brendel, "Tumor Therapy with Shock Waves Requires Modified Lithotripter Shock Waves," Naturwissenschaften, No. 76, 1989.

(List continued on next page.)

Primary Examiner—Manwel Mendez
(74) Attorney, Agent, or Firm—Olive & Olive, P.A.

(57) ABSTRACT

This invention discloses an apparatus and method for producing microcavitational activity in aqueous fluids for noninvasive macromolecule delivery into living cells. A standard electrohydraulic shock wave lithotripter is fitted with an adjustable ring reflector that shares the same foci as the standard lithotripter hemi-ellipsoidal reflector. A small portion of the spherical shock wave, generated by the spark discharge at the first focus (F1), is reflected and diffracted by the ring reflector, resulting in a weak preceding shock wave approximately 8.5 $\mu s$ in front of the lithotripter shock wave reflected and diffracted by the hemi-ellipsoidal reflector. The peak negative pressure of the preceding weak shock wave or pulse at F2 can be adjusted from –0.96 to –1.91 MPa, using an output voltage of 25 kV. Living cells are exposed to the preceding shock wave and the lithotripter shock wave. With optimal pulse combination, the maximum efficiency of shock wave-induced cell membrane permeabilization can be enhanced substantially (up to 91%), by applying to the living cells a low dosage of, for example, 50 shocks. In addition, injury to mouse lymphoid cells is significantly increased at high dosage (up to 50% with shock number >100). The invention thus enables shock wave-inertial microbubble interaction to be used selectively to either enhance the efficiency of shock wave-mediated macromolecule delivery at low dosage or tissue destruction at high dosage.

46 Claims, 13 Drawing Sheets

OTHER PUBLICATIONS

A. Philipp, "Interaction of Lithotripter–Generated Shock Waves with Air Bubbles," No. 93, 1993.

Carles C. Church, "A Theoretocal Study of Cavitation Generated by an Extracorporeal Shock Wave Lithotripter," Journal of Acoustic Society of America, No. 86, 1989.

Andrew J. Coleman, John E. Saunders, "A Survey of Acoustic Output of COmmercial Extracorporeal Shock Wave Lithotripters," Ultrasound in Medicine & Biology, vol. 15 (No. 3), pp. 312–277, 1989.

Shiping Bao, Brian D. Thrall, Richard A. Gies, Douglas L. Miller, "In Vivo Transfection of Melanoma Cells by Lithotripter Shock Waves," Cancer Research, No. 58, pp. 219–221, 1998.

U. Lauer, E. Burgelt, Z. Squire, K. Messmer, PH Hofschneider, M. Gregor, M. Delius, "Shock Wave Permeabilization as a New Gene Transfer Method," Gene Therapy, No. 4, 1997.

M. Delius, PH Hofschneider, U. Lauer, K. Messmer, "Extracorporeal Shock Waves for Gene Therapy," The Lanclet, No. 345, 1995.

S. Gambihler, M. Delius, K.W. Ellwart, "Permeabilization of the Plasma Membrane of L1210 Mouse Leukemia Cells Using Lithotripter Shock Waves," Journal of Membrane Biology, No. 141, pp. 267–275, 1994.

M. Delius, "Medical Applications and Bioeffects of Extracorporeal Shock Waves," Shock Waves, (Nov. 23, 1994).

↑ 202 μs  ↑ 222 μs

APPARATUS AND METHOD FOR MACROMOLECULE DELIVERY INTO LIVING CELLS

This invention was made with government support under Grant No(s). CCR-92-16122 & CCR-90-57570 awarded by the National Science Foundation and Grant No. N00014-94-1-1086 awarded by the Office of Naval Research. The government has certain rights in the invention.

This invention was made with Government support under Grant No. HD33760 awarded by the National Institutes of Health and BES-9704960 awarded by the National Science Foundation. The Government has certain rights in the invention.

FIELD OF THE INVENTION

The present invention relates to an apparatus and method for producing microcavitational activity in aqueous fluids causing transient cell membrane permeabilization of living cells so as to promote macromolecule delivery into such living cells.

BACKGROUND OF THE PRIOR ART

Shock wave lithotripsy (SWL) has traditionally been used to treat kidney stone disease. There exist various devices and methods for generating high-intensity, focused shock waves for the fragmentation of concretions, such as kidney stones, inside a human being and confined in a body liquid. U.S. Pat. No. 3,942,531 of Hoff et al. discloses the use of a spark gap discharge in water to generate a shock wave within an ellipsoidal reflector which couples and focuses the shock wave to fragment kidney stones inside the body. Hahn et al. in U.S. Pat. No. 4,655,220, disclose a device using a coil and a mating radiator, in the form of a spherical segment, to produce magnetically induced self-converging shock waves. Wurster et al. in U.S. Pat. Nos. 4,821,730 and 4,888,746, disclose the use of piezoelectric elements arranged in mosaic form on a spheroidal cap to produce focused high-intensity shock waves at the geometric center of the cap, where the concretion must be placed. Other techniques for generation of shock waves for use in medicine include optical sources such as lasers, high-velocity projectiles, and localized explosive devices.

Inspired by the success of shock wave lithotripsy in the treatment of kidney stone disease, significant efforts have been made to explore a broad spectrum of shock wave applications in medicine. Lithotripter-generated shock waves have been investigated for potential use in tumor therapy, fracture healing of bones, treatment of tendinitis, and ablation of liver tissues with various degree of success.

It has also been shown that at low dosage ("low dosage" is defined for the purpose of this application as a low number of shock waves), lithotripter shock waves or pulses can cause a transient increase in cell membrane permeability without killing the cells. (It is recognized that the term "shock wave" is sometimes used herein interchangeably with the term "pulse.") In this regard, the invention recognizes that shock waves may facilitate the transfer of macromolecules into target cells and thus could potentially provide a non-invasive physical method for drug delivery and gene transfer. The invention also recognizes that enhanced cytotoxicity of several anticancer drugs in vivo by SWL may indeed benefit from shock wave-induced transient membrane permeability.

A typical or standard lithotripter pressure waveform (also referred to herein as a standard lithotripter shock wave) at the lithotripter focus consists of a leading shock front (compressive wave) with a peak positive pressure up to 100 mega Pascal's (MPa), followed by a tensile (negative) phase with a peak negative peak pressure up to 10 MPa, and a total pulse duration of 3 to 7 $\mu$s. It is also known that the negative phase of an incident shock wave can induce transient cavitation bubbles in the focal region, if the tensile stress exceeds about 1 MPa.

Using the Gilmore model for bubble dynamics, Church has shown that a cavitation nucleus (1~10 $\mu$m in radius) in water impinged by a lithotripter shock wave will be initially compressed by the leading shock front, and then expanded by the ensuing tensile wave into a bubble of 1~3 mm in diameter in a few hundred microseconds. Subsequently, the expanded bubble will undergo a violent inertial collapse, generating high temperature (up to 10,000 K) inside the collapsed bubble and secondary shock wave emission into the surrounding fluid. Following this primary collapse, the bubble will oscillate (rebound and then collapse again) several times with exponentially decreased amplitude before it eventually reaches a size of about 40 $\mu$m due to rectified gas diffusion. The basic features of such a characteristic bubble oscillation has been confirmed experimentally, using simultaneous high-speed photography and acoustic emission measurements. During SWL, if bubbles generated by the earlier shock waves were to be stabilized on a tissue surface, the interaction of such a stable bubble with a subsequent lithotripter pulse may generate a liquid jet along the wave propagation direction, provided that the size of the bubble is within a certain range (250 $\mu$m<$R_{b0}$<750 $\mu$m, for a XL-1 lithotripter) as discussed in: A. Philipp, M. Delius, C. Scheffczyk, A. Vogel, and W. Lauterbom, *Interaction Of Lithotripter Generated Shock Waves In Bubbles,* J. Acoust. Soc. Am. 93;2496–2509 (1993), which is deemed incorporated herein by reference.

Also recognized by the invention is the belief that the shear stresses, and secondary shock wave emission and jet impact associated with the rapid expansion and collapse of cavitation bubbles may contribute to the bioeffects produced by SWL. When cavitation activity in the culture medium is suppressed by excessive ambient pressure, SWL-induced cell injury and membrane permeability change can be significantly inhibited. In contrast, when cavitation activity in vivo is enhanced by intravenous injection of ultrasound contrast agents (well-known cavitation nuclei) immediately before SWL, the vascular injury produced in animal models is substantially increased, even at low-pressure amplitudes ineffective for stone fragmentation. These findings are recognized by the invention to clearly demonstrate that cavitation is an important mechanism for SWL-induced bioeffects.

Despite all this evidence, the pressure waveform and associated cavitational activities produced by current shock wave lithotripters may not be optimal for tumor treatment and macromolecule delivery. Several studies have shown that an air-water interface near the lithotripter focus can dramatically enhance SWL-induced bioeffects on cells and small tumors. This observation had led some investigators to suggest that a different shock waveform is needed for tumor therapy. Moreover, the transfection efficiency of shock wave-mediated gene transfer is currently low compared to other established methods, and air injection into the target cells was found to be necessary to enhance the transfection efficiency in vivo. Flotte et al, in U.S. Pat. No. 5,614,502, disclose use of compounds in combination with a series of high-pressure transients for delivery of such compounds into cells. However, Flotte et al use a high-pressure shock wave without controlling the resulting cavitation, resulting in high cell death. With this in mind, the present invention recognizes that the ability to control the formation and subsequent bubble oscillations is critical for producing optimal bioeffects by SWL. However, because of the temporal profile and the low pulse repetition rate of current lithotripter shock waves, the invention also recognizes that the collapse of SWL-induced cavitation bubbles is uncontrolled and is predominantly influenced by the inertial effect of the surrounding fluid. Furthermore, what is also recognized is that because of the limited fluid-filled space in tissue and in blood vessels, the expansion of SWL-induced cavitation bubbles in vivo can be severely constrained, and thus the resultant bioeffects are less dramatic as compared to in vitro conditions.

With the foregoing in mind, it becomes a general object of the present invention to provide an apparatus and method for delivery of macromolecules into living cells.

It is a further object of the present invention to provide an apparatus and method for applying to living cells a first low-pressure shock wave followed a few microseconds later by a high-pressure shock wave in order to facilitate delivery of macromolecules into the living cells.

It is another object of the present invention is to provide an ellipsoidal reflector for current electrohydraulic shock wave lithotripters that generates a first low-pressure shock wave followed a few microseconds later by a high-pressure lithotripter shock wave.

It is a further object of this invention to provide an ellipsoidal reflector that generates a first low-pressure shock wave followed a few microseconds later by a high-pressure lithotripter shock wave such that the peak pressure of the first shock wave may be varied.

It is yet another object of the present invention to use a preceding weak shock wave to induce inertial microbubbles in front of a high-pressure lithotripter shock wave.

It is still another object of the present invention to control the size and distribution of microbubbles in order to facilitate the delivery of macromolecules into living cells.

Another object of this invention is to provide an apparatus and method for manipulating shock wave and microbubble interaction to selectively improve the efficiency of shock wave-mediated macromolecule delivery and tissue ablation.

Other objects and advantages will be more fully apparent from the following disclosure and appended claims.

SUMMARY OF THE INVENTION

In the preferred embodiment of the present invention, an ellipsoidal reflector of the present invention is used in an electrohydraulic shock wave lithotripter to generate a weak low-pressure shock wave that precedes a high-pressure shock wave by a few microseconds. The preceding shock wave induces inertial microbubbles, which expand to a maximum size ranging approximately from 100–200 $\mu$m before being collapsed by the ensuing high-pressure shock wave. This in situ shock wave-inertial microbubble interaction generates strong secondary wave emission immediately following the high-pressure shock wave and the formation of microjets along the wave propagation direction. In another aspect of the invention, the ellipsoidal reflector may be modified to vary the positive and negative pressure wave forms of the low and high pressure shock waves to enhance the efficiency of membrane permeabilization at low dosage and to increase cell damage at high dosage.

DETAILED DESCRIPTION OF PREFERRED EMBODIMENTS OF THE INVENTION

A. Design and Methods

1. Shock Wave Reflector of the Invention

Figure 1:
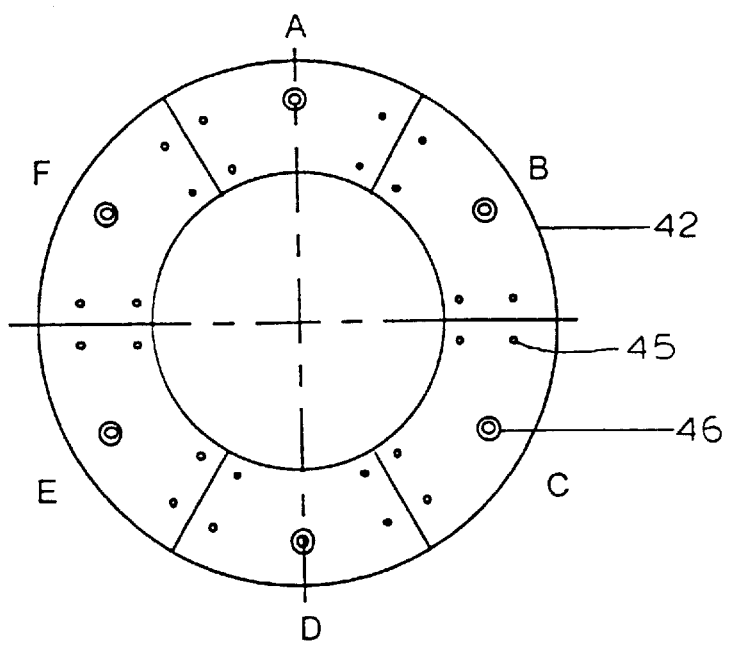
FIG. 1 is a top view of the ring reflector of the present invention.
Figure 2:
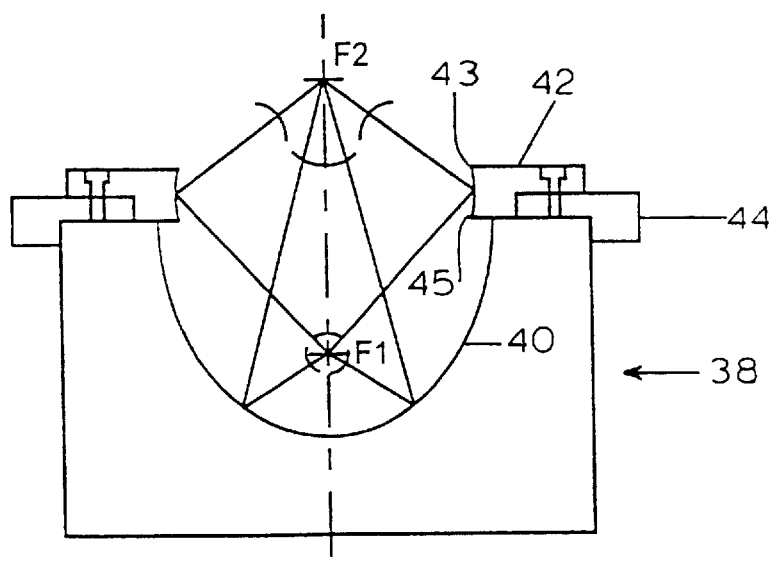
FIG. 2 is a side cross sectional view of the staged double ellipsoidal reflector of the present invention, incorporating the ring reflector of FIG. 1.

Referring to FIG. 2, a standard truncated ellipsoidal reflector 40 typically used in electrohydraulic shock wave lithotripters is used to focus the shock wave, generated by a spark discharge at the first focus (F1), onto the second focus (F2) of the reflector, typically where the target kidney stones or living cells are located. The propagation time of the shock wave is determined by the ratio of the major axis of the ellipsoidal reflector and the shock wave propagation speed in water. Two ellipsoids can share the same foci (F1 and F2), but have different major and minor axes. Uniquely, the present invention, illustrated in FIGS. 1 and 2, uses a ring reflector 42 in combination with the original reflector 40 to form a staged double ellipsoidal reflector 38 as shown in FIG. 2. Ring reflector 42 can be made of brass or other materials of high acoustic impedance as is known in the art. Ring reflector 42 is connected, via an adapter ring 44, to the reflector rim of reflector 40. Ring reflector 42 is comprised of six separable identical segments A, B, C, D, E, and F as shown in FIG. 1. Each component is attached to the adapter ring 44 by screws 45. Position pins 46 are used to correctly align ring reflector 42 with original reflector 40. It is understood that in accordance with the present invention, the different ring reflector 42 configurations operate in conjunction with the standard hemi-ellipsoidal reflector 40 to form the stage double ellipsoidal reflector 38.

In the preferred embodiment, a Dornier XL-1 experimental lithotripter is used. The Dornier XL-1 lithotripter uses an 80 nF discharge capacitor (not shown) and a hemi-ellipsoidal reflector 40 (also referred to herein as an "original reflector") with a semi-major axis $a=110.3$ mm, semi-minor axis $b=78$ mm, and a half-focal length $c=78$ mm. In comparison, the inner surface of ring reflector 42, connected to the ellipsoidal surface of original reflector 40, has a semi-major axis $a=102.8$ mm, semi minor axis $b=67$ mm, and a half-focal length $c=78$ mm. While being confocal, the major axis of ring reflector 42 is 15 mm shorter than that of original reflector 40, corresponding to a reduction of $\sim 10$ $\mu$s in acoustic wave propagation time (for reflected waves) from F1 to F2.

FIG. 2 also illustrates that an initial spherically divergent shock wave generated at F1 will be reflected partially from the reflecting surface of original reflector 40 and partially from the reflecting surface of ring reflector 42. While both reflected shock waves converge to F2, they are temporally separated by a time delay determined by the difference in the major axes of the original and the ring reflectors 42. Thus, that portion of the initial shock wave reflected by ring reflector 42 precedes that portion of the initial shock wave reflected by original reflector 40, i.e., the ensuing shock wave or lithotripter shock wave (LSW). The preceding and lithotripter shock waves are also referred to herein as first and second pulses, respectively.

This short time delay was chosen according to the invention to allow the inertial cavitation bubbles, induced by a low pressure preceding shock wave reflected from ring reflector 42, to grow to a size of a few hundred microns before being collapsed by the ensuing high-pressure shock wave. In order to adjust the intensity of the preceding shock wave, ring reflector 42 was fabricated into six identical segments A, B, C, D, E and F (thickness=28 mm), with each segment connectable to adapter ring 44 via position pins 46 and screws 45 as discussed above and as illustrated in FIG. 1. Ring reflector 42 shadows only a small portion ($\sim 5^0$ steradian) of the original reflector 42, and thus would not affect the high-pressure lithotripter shock wave reflected by the original reflector 40 significantly. Therefore, according to the present invention, various pressure intensity combinations of the preceding and lithotripter shock wave series are produced depending on the annular ring 42 configuration used. The following ring reflector 42 configurations of the invention are D2, D3, and D6 comprised of segments A, D; A, C, E; and A, B, C, D, E, F, respectively. Although the preferred embodiment uses a ring reflector 42 in combination with a standard lithotripter hemi-ellipsoid reflector 40, it is understood in the art that the standard lithotripter hemi-ellipsoidal reflector 40 can be modified in a number of different ways to generate first and second pulses having the same $F_2$, but different travel time to $F_2$. Furthermore, it is also understood that the first and second pulses may be produced by various other devices known in the art, e.g., lasers, piezoelectric and electromagnetic shock wave generators, high velocity projectiles, and localized explosive devices as mentioned above.

Figure 3:
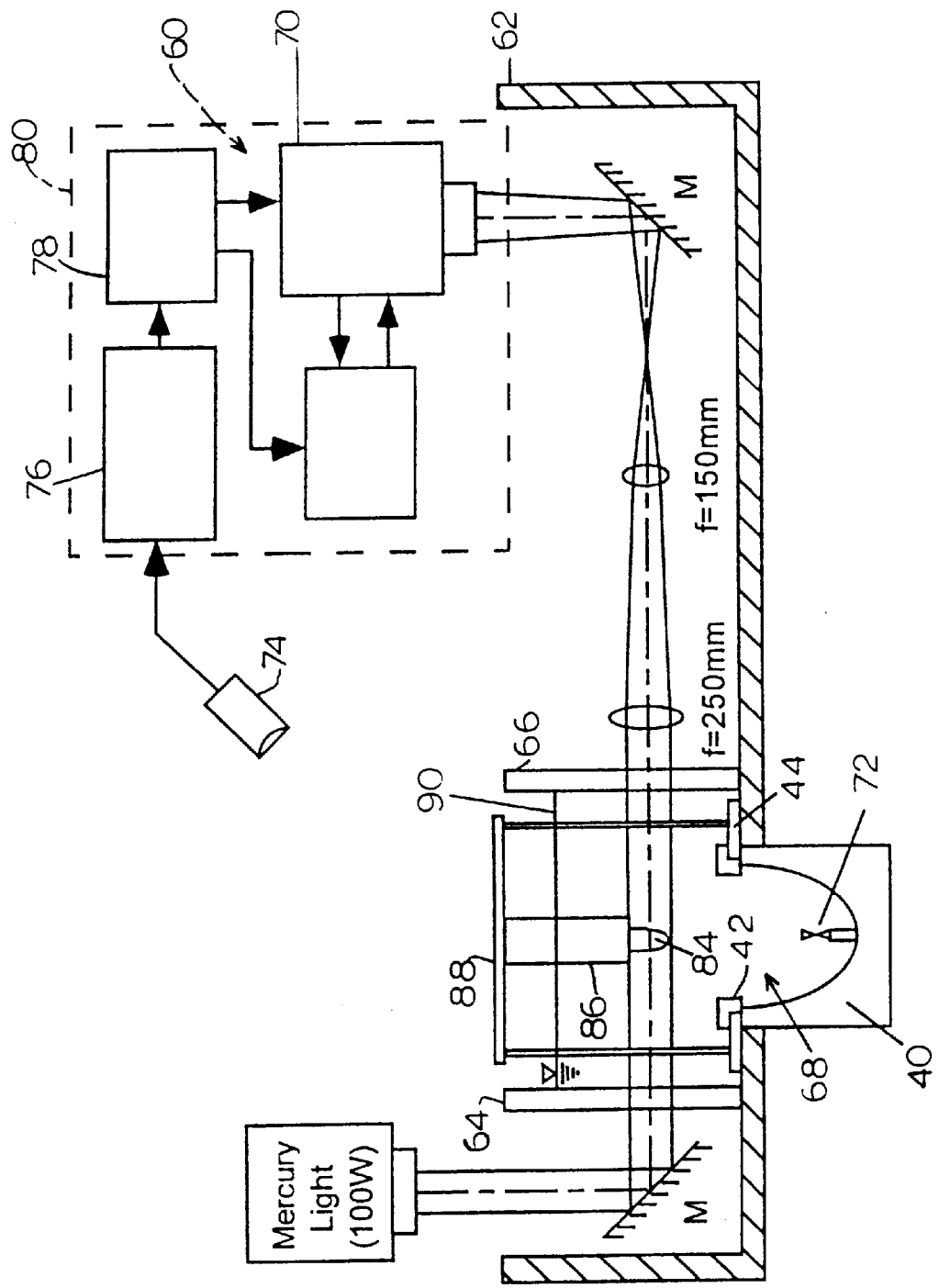
FIG. 3 is a schematic diagram showing a high-speed shadowgraph imaging apparatus and the water tank of a XL-1 lithotripter, equipped with the reflector of the invention.

2. Physical Characterization of Shock Wave-Inertial Microbubble Interaction a. Pressure measurements: The acoustic field around the beam focus of the lithotripter was measured using a hydrophone system with disposable PVDF (polyvinylidene difluoride) membranes (Sonic Industries™). The disposable PVDF membrane (25 μm thick) has a sensing area of <1 mm, connected to gold electrodes deposited on the surface of the membrane. During shock wave exposure in water, the electrode leads are gradually eroded by cavitation, resulting in an increase of lead resistance and a concomitant reduction of the membrane sensitivity. To ensure the integrity of the hydrophone, the resistance of the lead electrodes was monitored during the course of pressure measurements. According to manufacturer's specification, when the change in lead resistance exceeded 200Ω, the PVDF membrane was replaced. The operation of the hydrophone system used in the present invention is explained in detail in Sonic Industries™, *Reference Shockwave Hyarophone System™, User's Manual*, Version 1.2, 1997, which is deemed incorporated herein by reference. To further protect it from cavitation damage and to ensure adequate frequency response, the original PVDF membrane was encapsulated in castor oil. This was done by filling up the space enclosed by the supporting frame of the PVDF membrane with castor oil and then sealed it with a 115 μm thick polyester membrane sheet. Care was taken to avoid trapping air bubbles inside the castor oil enclosure, which has a total thickness of about 8 mm, with the PVDF membrane located at the middle plane. The encapsulated PVDF membrane was then calibrated by comparison with the output from a calibrated PVDF needle transducer (MHA9-6, FORCE INSTITUTE) in the acoustic field of a 2.5 MHz focused transducer (Panametrics™). For acoustic field mapping of the lithotripter, the PVDF membrane was attached to a x-y-z translational stage (0.01-mm precision), and scanned both along and transverse of the shock wave axis at F2. Triplicate of measurements were made at each location, with the pressure waveforms registered on a LeCroy™ digital oscilloscope (Model 9314) operated at 100 MHz sampling rate, corresponding to a minimal time interval of 10 ns/point.

b. High-speed photography: Referring to FIG. 3, to visualize shock wave propagation, bubble dynamics, and shock wave-bubble interaction, a shadowgraphic imaging system 60 was set up inside the original water tank (10"×25"×39", H×W×L) 62 of the lithotripter. Two half-inch thick lucite plates 64, 66 were used to form a small water enclosure (10"×13"×25", H×W×L) around the shock wave generator 68, so that a higher image magnification is achieved. High-speed shadowgraphs were recorded using an ICCD (intensified CCD) camera (4 Quik 05A, Stanford Computer Optics) 70 with an exposure time of 20 ns, corresponding to a spatial resolution of 30 μm. To provide a reliable time reference of the event, the spark discharge of the lithotripter electrode 72 was picked up by a fast photodetector 74 with a rise time of 35 ns (PDA50, Thorlab Inc.) and fed into the LeCroy™ oscilloscope 76. The synchronized output of the scope was then relayed to a digital delay generator (DS535, Stanford Research Systems) 78 which is used to control the electronic shutter (i.e. the intensifier) of the ICCD camera 70. By adjusting the delay time with respect to the spark discharge, a series of high-speed shadowgraphs can be recorded at different stages of shock wave propagation and subsequent bubble oscillations. To prevent interference from the electromagnetic noise generated by the lithotripter, a Faraday enclosure 80 was built to cover camera 70, and the trigger and control instruments.

c. Acoustic emission measurements: Acoustic emission, emanating from the beam focus of a lithotripter, was measured using a passive cavitation detection system described in the publication P. Zhong, I. Cioanta, F. H. Cocks, and G. M. Preminger, *Inertial Cavitation And Associated Acoustic Emission Produced During Electrohydraulic Shock Wave Lithotripsy*, J. Acoust. Soc. Am. 101,2940–2950 (1997), which is deemed incorporated herein by reference. Briefly, a focused hydrophone of 1 MHz resonant frequency and 101.6 mm focal length was aligned perpendicularly to the lithotripter axis, and confocally with F2. The output signal of the hydrophone was fed into a high-pass filter with 0.3 MHz cut-off frequency and a broadband amplifier (5052 PR Pulser/Receiver, Panametrics™) before registered on the LeCroy™ oscilloscope 76. It has been shown previously that the acoustic emission signal associated with lithotripter shock wave-induced cavitation oscillation has a unique double-burst structure. The first burst corresponds to the initial compression and subsequent expansion of cavitation nuclei by the incident lithotripter shock wave, and the second burst corresponds to the primary collapse of the bubble cluster. Hence, acoustic emission measurements were used to assess the overall dynamics of the bubble oscillation and also to correlate with the high-speed shadowgraph images.

3. Bioeffects Study

Mouse T-cell hybridoma DO-11.10 provided by Dr. P. Marrack (National Jewish Center for Immunology and Respiratory Medicine) were used. These cells were grown to confluent (2~4 million cells/ml) in T-75 culture flasks (Corning Costar™, Corp.) at 37° C. in Eagle™ medium containing 10% fetal bovine serum under a humidified atmosphere with 5% $CO_2$. FITC-labeled dextran (average molecule weight: 70 kD, Sigma Chemical Inc.), which are normally not taken up by cultured cells, were added to the suspended cell culture and adjusted to a final concentration of 1 mg/ml shortly before SWL treatment. After mixture, the cell suspensions containing FITC-Dextran were loaded into 1.5-mi polyethylene pipettes (VWR Scientific Products) with a bulb of 20 mm long and 10 mm in diameter. The culture medium was filled up to the tip of pipette 84, which is about 10 cm above the center of the bulb. Referring again to FIG. 3, the pipette 84 was fitted snugly into a Delrin holder 86 and connected to a supporting platform 88. This arrangement was used to ensure that the center of pipette bulb 84 is aligned consistently with F2 during the whole SWL procedure. The small enclosure surrounding the shock wave generator was filled with degassed and deionized water ($O_2$ concentration: <4 mg/L) $0_0$ up close to the level of the pipette tip. The water temperature was maintained at 35~37° C. by continuous circulation. Various numbers of shock waves generated at 25 kV output setting were delivered to pipette 84 in the treatment group at 1 Hz pulse repetition rate. Control groups were prepared following the same procedure and placed in the water tank 62 away from the lithotripter shock wave (LSW).

Following shock wave treatment, the cell culture was spun in a 15 ml capped tube and then washed with the culture medium. After repeating this process twice, the cells were re-suspended in 0.5 ml of the culture medium. Peamibilization efficiency was determined by Differential Interference Contrast Microscopy (DIC) and fluorescence microscopy, using a Zeiss Axioplan microscope. The cells that remain morphologically intact and are fluorescence-positive were counted. Cell mortality, defined as the percentage of cells that are morphologically damaged (lysed and membrane rupture), was measured by counting the number of intact cells in reference to the controlled group. In addition, functional impairment of the survival cells was assessed by staining with 0.1% trypan blue, a vital dye that is only taken up by cells undergoing necrosis. Combined results of these two tests, cell injury (defined as cells that are either physically damaged or functionally impaired) was determined.

4. Statistical analysis

Paired student-t test was used to determine statistically significant differences ($p<0.05$) between the results produced by the standard and modified lithotripter shock waves.

B. Results

Figure 4:
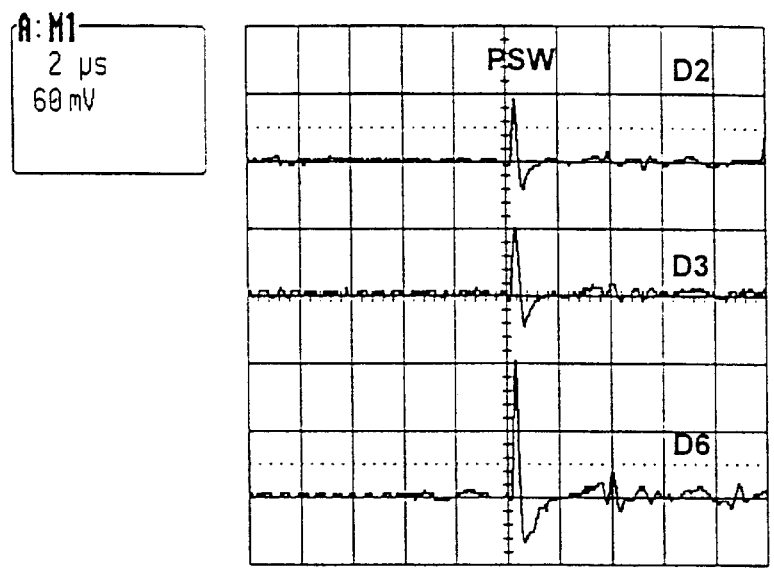
FIG. 4 is a graph showing the waveforms generated by different ring reflector arrangements (D2, D3, and D6) of the invention at 25 kV.
Figure 5:
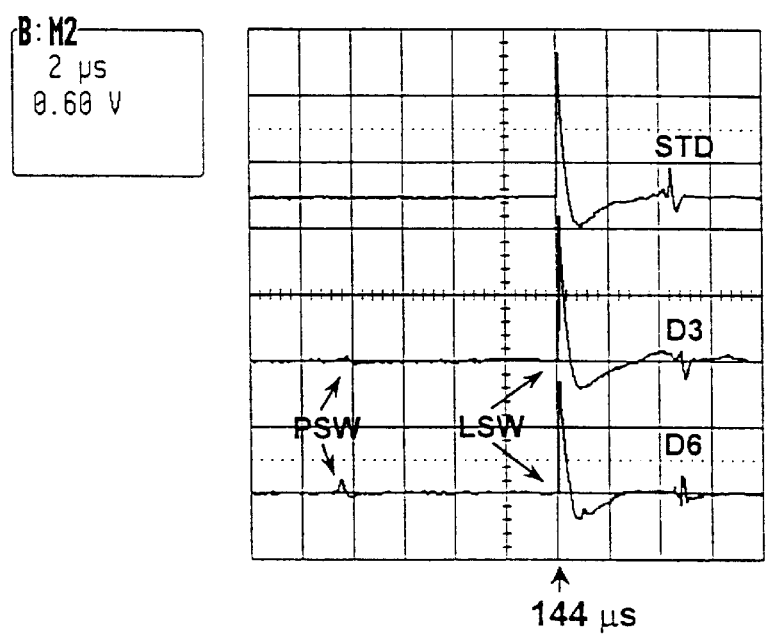
FIG. 5 is a graph showing the waveforms produced by a standard lithotripter reflector (STD), and the preceding shock wave forms followed by their respective high pressure lithotripter shock wave forms generated by the staged double ellipsoidal reflector of the present invention.

1. Physical characterization a. Pressure waveforms and distribution: Examples of pressure waveforms generated at F2 using different ring reflector configurations of the present invention are shown in FIGS. 4 and 5. Referring to FIG. 5, with the original reflector 40, a single lithotripter shock wave (LSW) was recorded about 144 $\mu$s after the spark discharge. In comparison, using the staged double ellipsoidal reflector 38 of the invention, a standard lithotripter shock wave (LSW) and a weak shock wave preceding the lithotripter shock wave (PSW) by approximately 8.5 $\mu$s were recorded. Due to a higher propagation speed of the shock wave, the arrival time of the lithotripter shock wave (LSW) at F2 and the time delay between the preceding shock wave (PSW) and the lithotripter shock wave were slightly reduced from the values (147 and 10 $\mu$s, respectively) calculated based on acoustic wave propagation. Compared to the lithotripter shock wave, the preceding shock wave (PSW) has a similar temporal profile, but much smaller pressure amplitudes. In addition, as the surface area of the annular ring reflector of the present invention increases (from D2 to D3, to D6), the preceding shock wave becomes stronger (FIG. 4) while the ensuing lithotripter shock wave (reflected from the surface area of the standard truncated ellipsoidal reflector 40) becomes weaker (FIG. 5).

Figure 6:
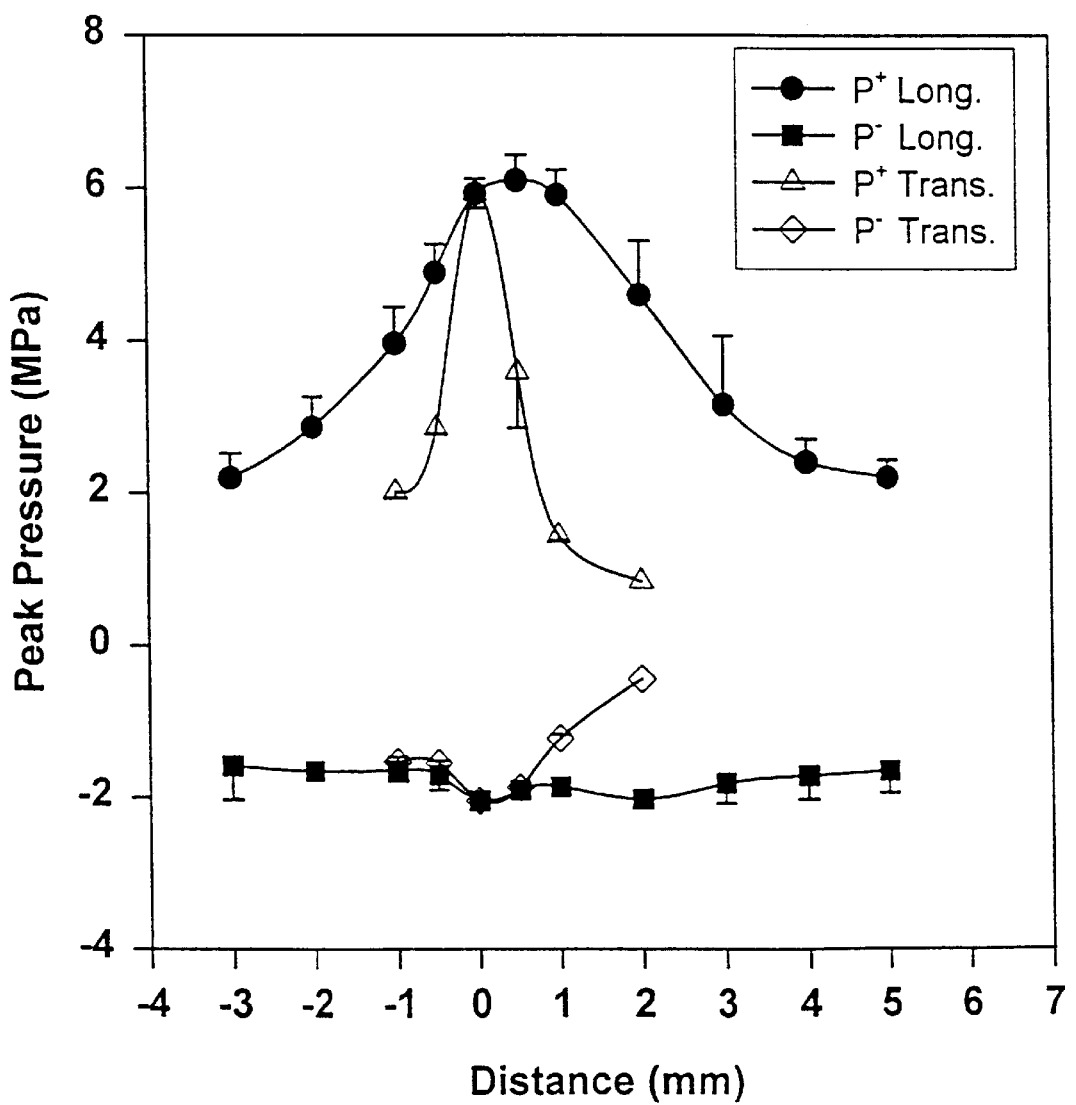
FIG. 6 is a graph showing peak pressure distributions of the preceding shock wave generated by the D6 ring reflector configuration of the invention at 25 kV.
Figure 8:
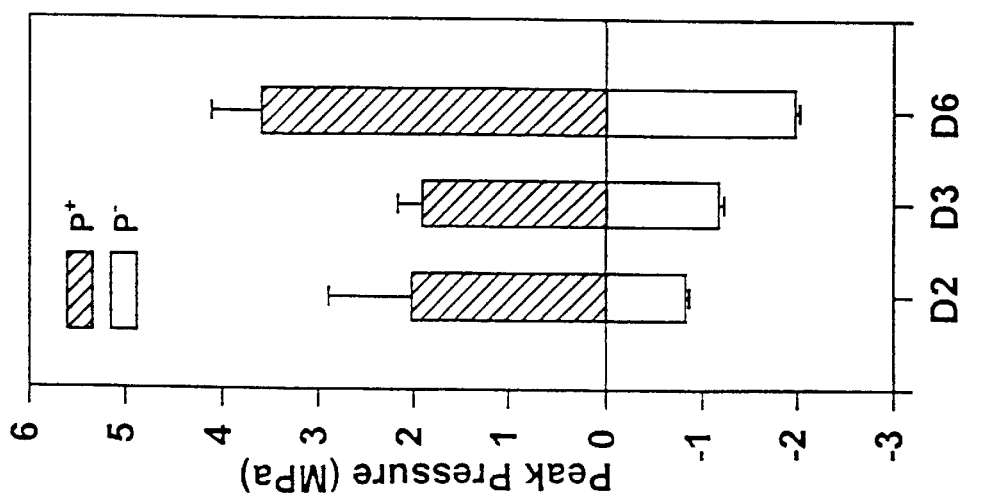
FIG. 8 is a graph showing the peak pressure of the positive and negative phases of the preceding shock waves produced by the different ring reflector configurations of the present invention at 20 kV.

The pressure distribution of the strongest preceding shock wave generated by reflector configuration D6 is shown in FIG. 6. The maximum pressure was measured slightly (~0.5 mm) beyond F2, along (longitudinal) and transverse to the major axis of the reflector. At F2 (identified as 0 mm in FIG. 6), a peak positive pressure ($P^+$) of 5.53 MPa and a peak negative pressure ($P^-$) of −1.91 MPa were recorded. Using the positive pressure curve, the −6-dB beam size of the preceding pulse was determined to be 5×1.2 mm along and transverse of the major axis of the reflector, respectively. Maximum positive and negative pressure of the preceding shock waves produced by ring reflector configurations D2, D3, and D6 is also illustrated by FIG. 8.

Figure 7:
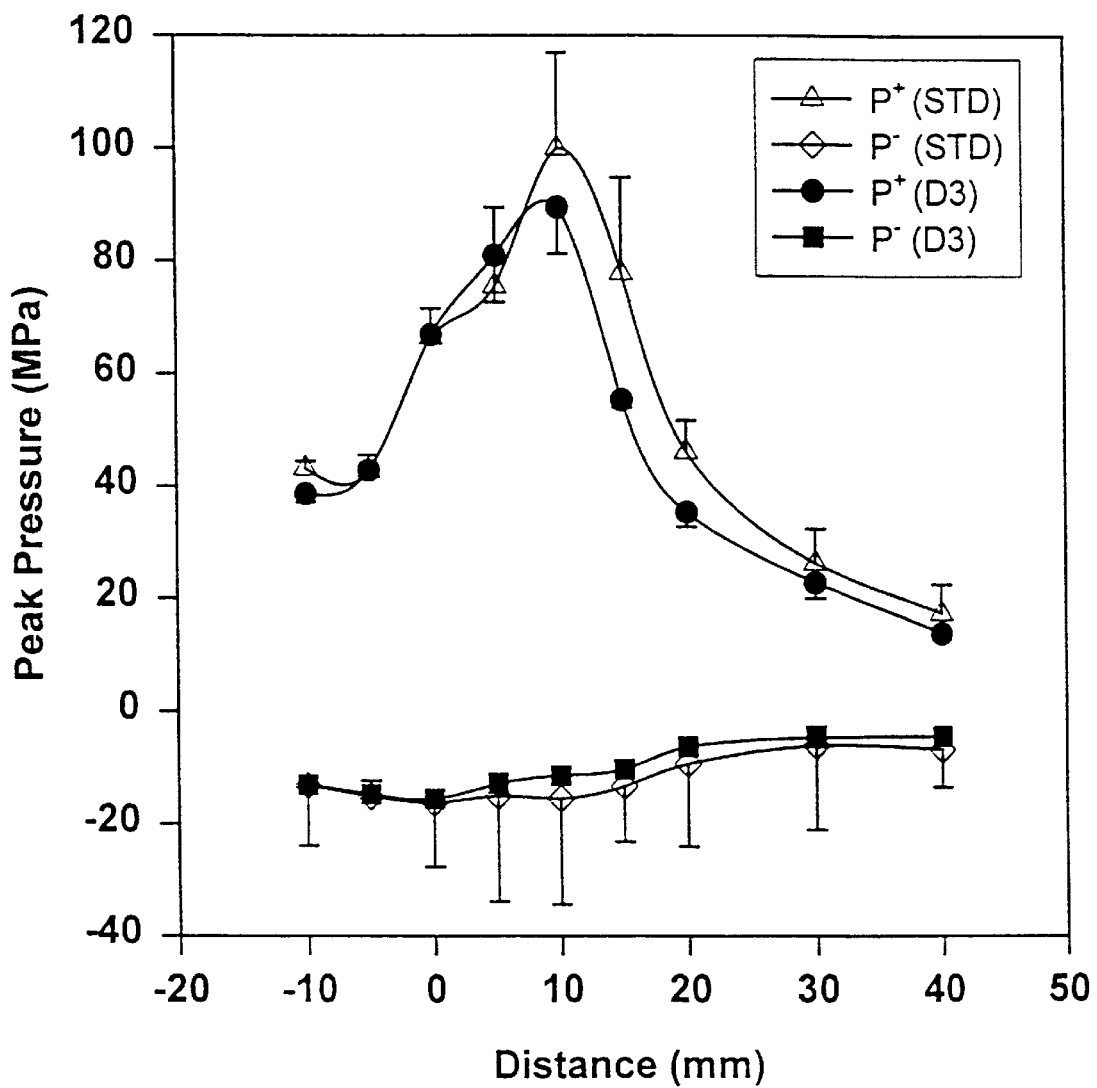
FIG. 7 is a graph showing the peak positive and negative pressure distributions of the standard lithotripter shock wave generated by the standard lithotripter reflector alone, and the peak positive and negative pressure distributions of the lithotripter shock wave when the D3 ring reflector configuration of the present invention is used, along the major axis of the ellipsoidal reflector at 25 kV.

In contrast and referring to FIG. 7, the maximum positive pressure of the lithotripter shock wave was measured about 10 mm beyond F2, for both the standard (100 MPa) and D3 (89.6 MPa) reflector configurations. This significant shift of the maximum positive pressure beyond F2 is caused by the nonlinear propagation of the lithotripter shock wave. At F2, the values of $P^+$ and $P^-$ of the lithotripter shock wave were measured to be 67.6 MPa and −17.6 MPa using the standard reflector 40, and 61.7 MPa and −15.2 MPa using the D3 reflector 42, respectively. The peak negative value, however, is consistently higher than the typical values measured in water ($<-10$ MPa), presumably due to the higher tensile strength of the castor oil that encloses the PVDF membrane. In addition, the maximum negative pressure of the lithotripter shock wave was measured at F2, instead of shifting closer to the shock wave source as reported from other lithotripters. The reason for this discrepancy is unknown. The −6-dB beam size of the lithotripter shock wave produced by original reflector 40 is 22×5 mm along and transverse to the lithotripter longitudinal axis, respectively. Similar beam sizes of the lithotripter shock waves (23×4 mm and 28×7 mm) were measured using the D3 and D6 reflector 42 configurations of the present invention. Table 1 summarizes the peak positive and peak negative pressure, and beam sizes of the preceding and lithotripter shock waves, produced by different reflector configurations.

TABLE 1

Peak Pressure at Lithotripter Focus and Beam Size

| Reflector Configuration | Preceding shock wave | | | Lithotripter shock wave | | |
|---|---|---|---|---|---|---|
| | $P^+$ (MPa) | $P^-$ (MPa) | Beam Size (mm) | $P^+$ (MPa) | $P^-$ (MPa) | Beam size (mm) |
| Standard | | | | 67.6 ± 4.49 | −17.6 ± 2.21 | 6 × 22 |
| D2 | 2.88 ± 0.48 | −1.1 ± 0.38 | | 61.7 ± 5.03 | −19.4 ± 3.36 | |
| D3 | 3.01 ± 0.32 | −0.96 ± 0.32 | | 61.7 ± 2.63 | −15.2 ± 2.71 | 4 × 23 |
| D6 | 5.53 ± 0.50 | −1.91 ± 0.23 | 1.2 × 5 | 56.9 ± 2.87 | −9.3 ± 3.08 | 7 × 28 |

The temporal parameters of the preceding and lithotripter shock waves are shown in Table 2 below. The rise time ($t_r$) of the shock front was measured by the time duration from 10% to 90% of P+. The positive ($t^+$) and negative ($t^-$) pulse duration of the shock waves were measured by the zero crossing duration of the positive and negative cycles, respectively. In general, the preceding shock wave has a longer rise time, but shorter pulse duration, compared to the lithotripter shock wave. In addition, for the ring reflector configurations D2, D3, and D6, the values of $t_r$, $t^+$, and $t^-$ for both the preceding and lithotripter shock waves all become larger as the surface area of the annular ring reflector increases. Of particular interest was that the rise time of lithotripter shock fronts generated by the ring reflectors was found to be longer than that produced by the standard reflector. This increased rise time seems to correlate with the reduced peak pressure of the lithotripter shock wave, which may be caused partially by the slightly reduced reflector surface area and partially by the scattering of lithotripter shock waves from the inertial microbubbles.

laterally along the shock front and cross on the central axis of the reflector. Due to nonlinear shock wave propagation, a Mach stem is typically formed beyond the geometric focus of the reflector. This observation is consistent with the shift of the peak positive pressure of the lithotripter shock waves, measured by the PVDF hydrophone.

Because of the temporal profile of the shock wave, cavitation bubbles are induced in the wake of the shock front where the tensile pressure is high. These bubbles expand initially to a maximum size of approximately 6~8 mm and then collapse violently, producing secondary shock wave

TABLE 2

Temporal Parameters of the Shock Waves

| Reflector Configuration | Preceding shock wave | | | Lithotripter shock wave | | |
|---|---|---|---|---|---|---|
| | $t_r$(ns) | $t^+$($\mu$s) | $t^-$($\mu$s) | $t_r$(ns) | $t^+$($\mu$s) | $t^-$($\mu$s) |
| Standard | | | | 20 ± 4.4 | 0.82 ± 0.27 | 3.83 ± 0.69 |
| D2 | 126 ± 31 | 0.37 ± 0.05 | 0.85 ± 0.26 | 24 ± 7.4 | 0.51 ± 0.05 | 1.77 ± 0.06 |
| D3 | 135 ± 22 | 0.38 ± 0.03 | 0.93 ± 0.16 | 27 ± 5.9 | 0.76 ± 0.29 | 2.76 ± 0.94 |
| D6 | 142 ± 39 | 0.48 ± 0.13 | 1.62 ± 0.57 | 38 ± 9.5 | 0.79 ± 0.24 | 3.01 ± 0.35 |

$t_r$: Rise time of the shock front, measured from 105 to 90% of the peak positive pressure.
$t^+$: Positive pulse duration, measured by the zero-crossing duration of the positive cycle of the shock wave.
$t^-$: Negative pulse duration, measured by the zero-crossing duration of the negative cycle of the shock wave.

Figure 9:
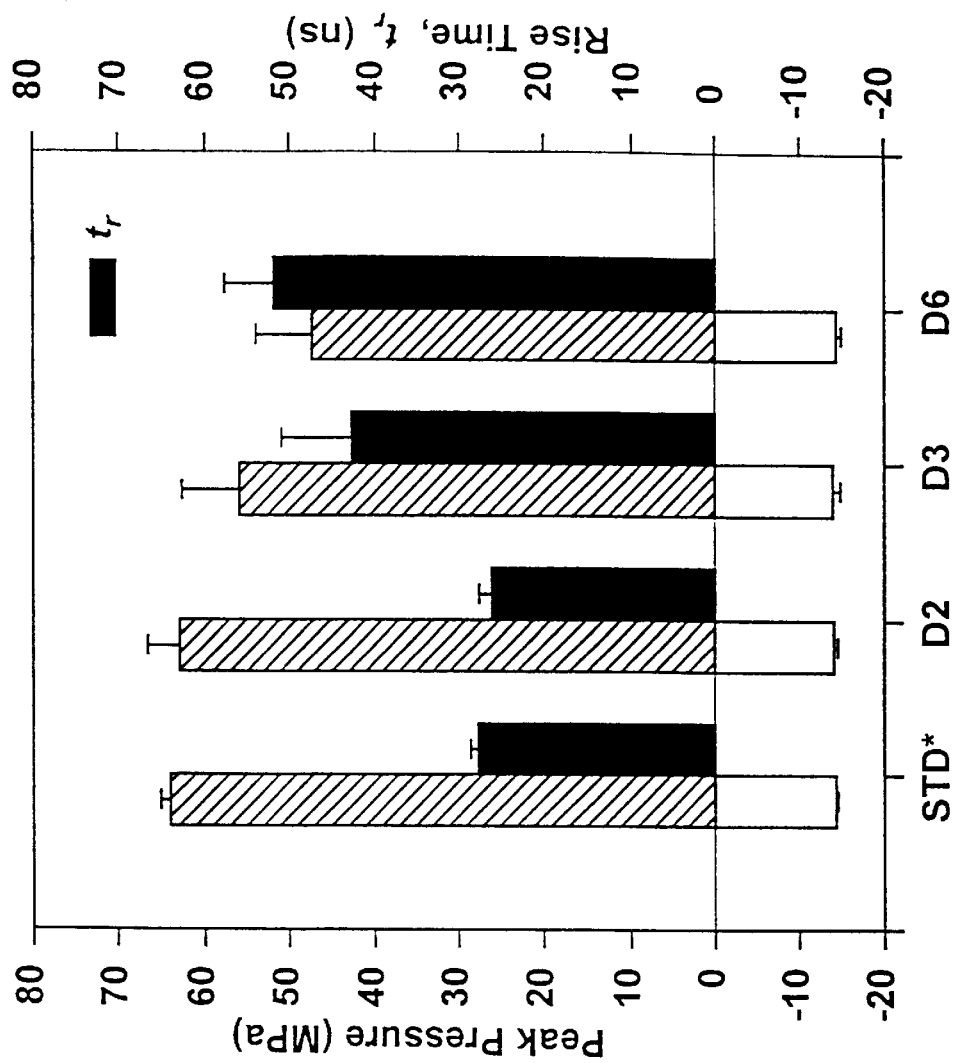
FIG. 9 is a graph showing the peak positive and negative pressure values and corresponding rise times produced by the standard lithotripter reflector and the different ring reflector configurations of the present invention at 20 kV.

Referring to FIG. 9, pressure measurements at 20 kV show that as the surface area of the ring reflector 42 increases (from D2 to D3, to D6), $P^+$ of the lithotripter shock wave (LSW) decreases significantly while $t_r$ increases substantially from the values corresponding to the original reflector. Since $P^-$ of the preceding shock wave also increases significantly from D2 to D6 (FIG. 8), the size and density of inertial microbubbles generated in front of the lithotripter shock wave should increase accordingly, resulting in a stronger shock wave-inertial microbubble interaction. Hence, these results indicate that the amplitude of the lithotripter shock wave (LSW) is influenced by the scattering of the lithotripter shock wave (LSW) from the microbubbles generated by the preceding pulse. Similar amplitude reduction and shock front thickening effects were also observed when lithotripter shock waves were scattered by stable glass beads suspended in castor oil.

It is also recognized by the present invention that the lithotripter shock wave, following the preceding shock wave, can be generated such that its tensile (negative) component is significantly reduced, which may also enhance control of the shock wave-inertial microbubble interaction. U.S. Pat. No. 5,800,365 of Pei Zhong et al. (the "'365 patent") discloses how to generate a shock wave having a reduced tensile component such that the shock wave does not induce cavitation. The 365 patent is hereby deemed incorporated herein by reference.

b. High-speed photography: As is known in the art, after spark discharge at the electrode, the standard ellipsoidal reflector 40 reflects shock waves having several important features (not shown). In summary, the original or lithotripter shock wave, moving toward F2, consists of a concave central part corresponding to the focused shock front and a convex part originated from the wave diffraction at the aperture of the reflector 40. The diffracted waves propagate emission, which are spherically divergent circular rings surrounding the collapsed bubbles. During the initial expansion, individual bubbles are nearly spherical and separated from each other. However, in the later stage of the expansion, significant bubble aggregation leads to the formation of large bubbles with various shapes. This aggregation process extends the duration of bubble expansion significantly.

Figure 10:
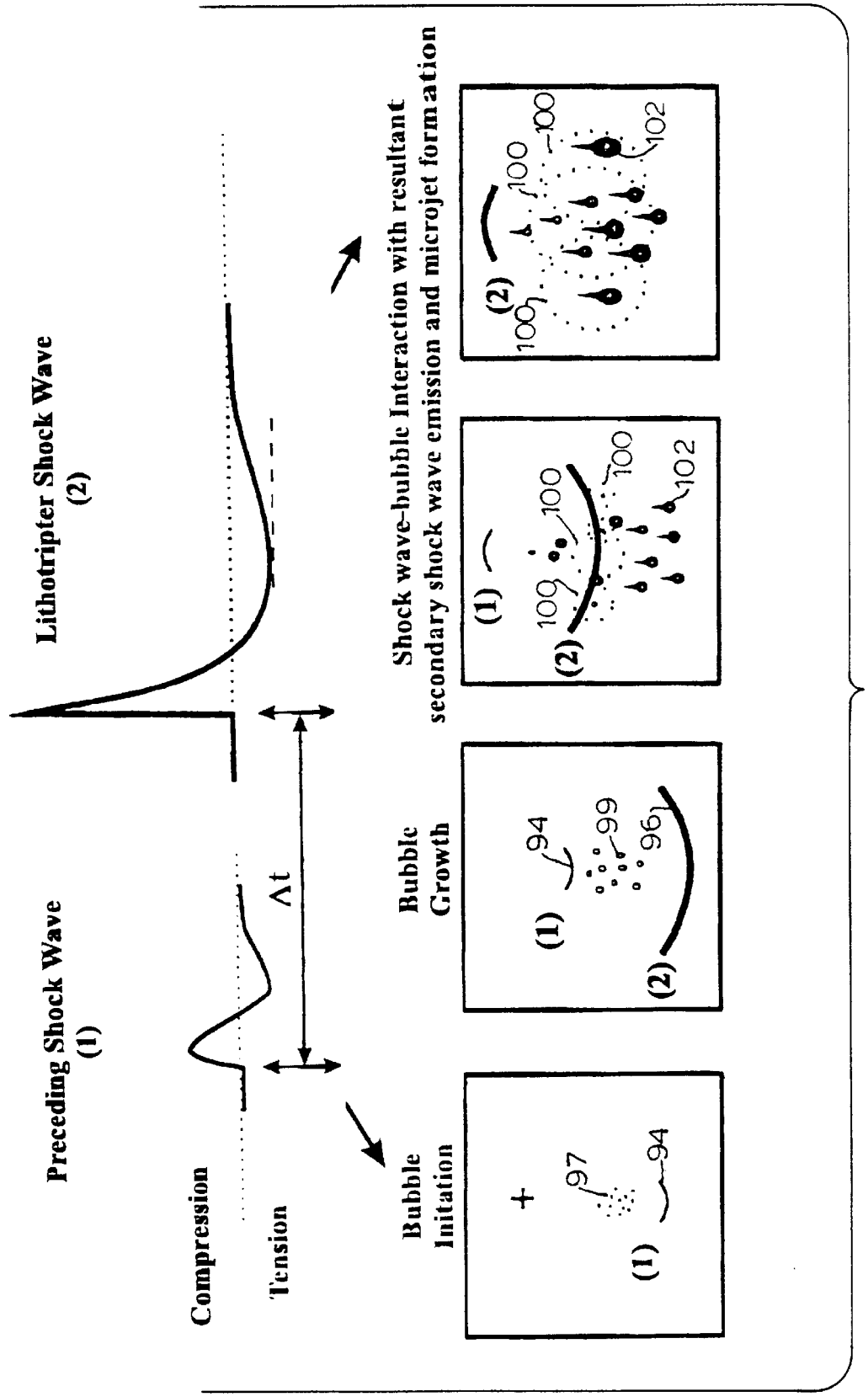
FIG. 10 is a schematic diagram of the shock wave-inertial microbubble interaction of the present invention.

When a staged double ellipsoidal reflector 38 of the present invention was used as shown in FIG. 10, three major differences in the high-speed shadowgraphs can be noticed. First, a preceding shock wave 94, produced by the reflection and diffraction of the incident shock wave from the ring reflector 42, was observed ahead of the lithotripter shock wave 96. Preceding shock wave 94 consists largely of diffracted waves from both the upper and lower rims 43, 45 of the ring reflector 42 (See FIG. 2), with both waves crossing on the central axis of the reflector. In addition, another weak shock wave (not shown) was also observed in between the preceding shock wave 94 and the lithotripter shock wave 96. This additional wave is speculated to correspond to the portion of the lithotripter shock wave 96 that is in the shadow of the ring reflector 42, which is accelerated while passing diagonally through ring reflector 40. Second, small inertial bubbles 99 are induced from cavitation nuclei 97 by the preceding shock wave 94, and expanded to a size of 100~200 $\mu$m before being collapsed in situ by the incident lithotripter (original) shock wave 96. Consequently, strong secondary shock wave emission was generated immediately following the propagating lithotripter shock front, as numerous circular rings collectively identified as 100. Third, the collapse of some inertial microbubbles by the lithotripter shock front appeared to be asymmetric, resulting in the formation of microjets 102 along the wave propagation direction. Following this initial collapse, most microbubbles rebounded and re-expanded again under the influence of the tensile stress of the lithotripter shock wave. These bubbles again reached a maximum size in several hundred microseconds and then collapsed rapidly, generating strong secondary shock wave emission.

Figure 12:
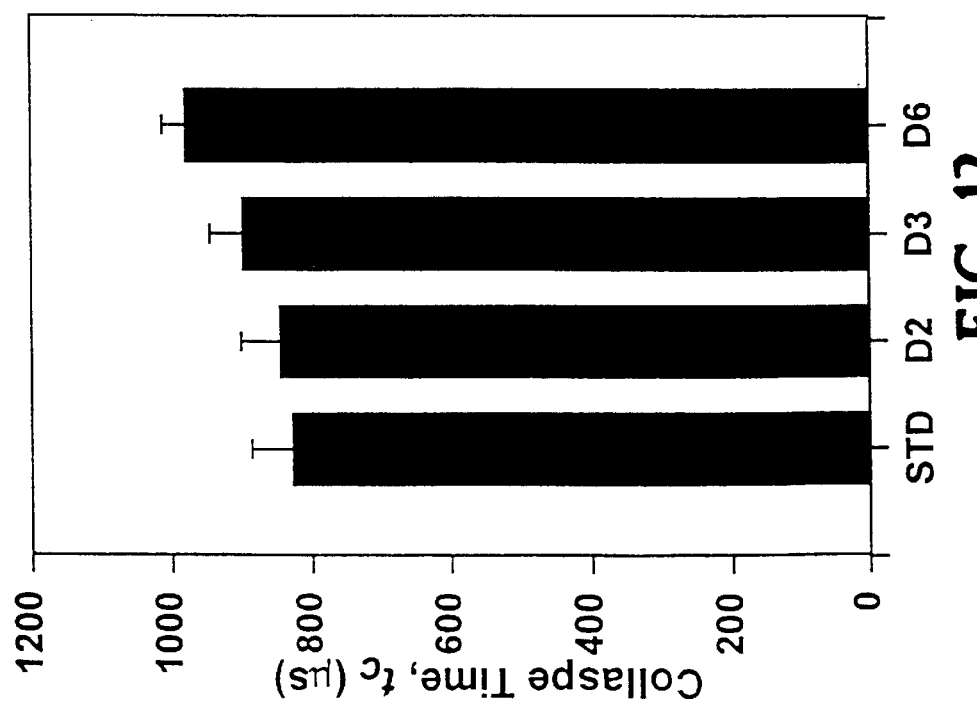
FIG. 12 is a graph showing collapse time ($t_c$) of the acoustic emission waveforms produced by the standard lithotripter reflector and the different ring reflector configurations of the present invention at 25 kV.
Figure 11:
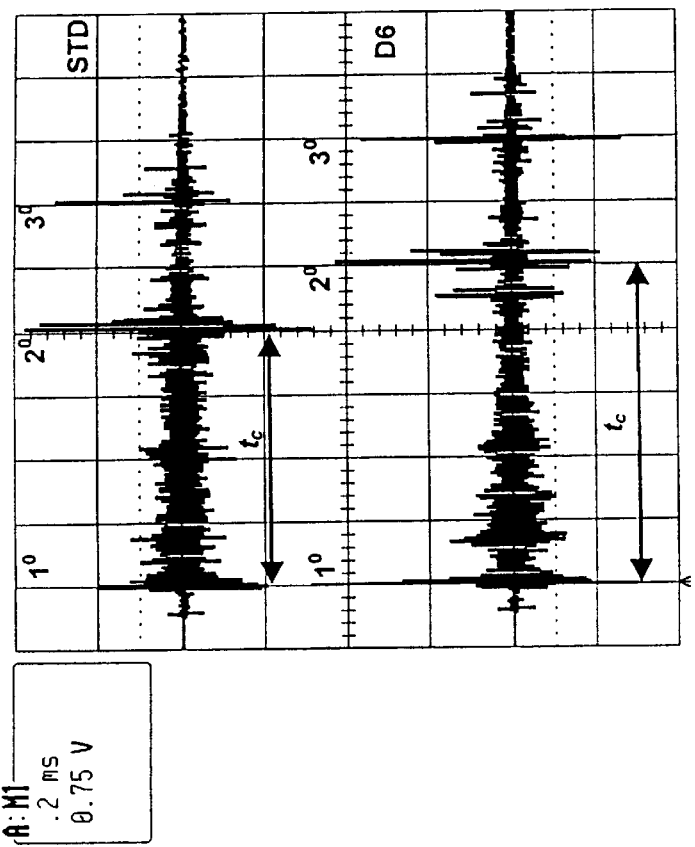
FIG. 11 is a graph showing the primary, secondary, and tertiary acoustic emission bursts produced by the standard lithotripter reflector and the D6 ring reflector configuration of the present invention at 25 kV.
Figure 13:
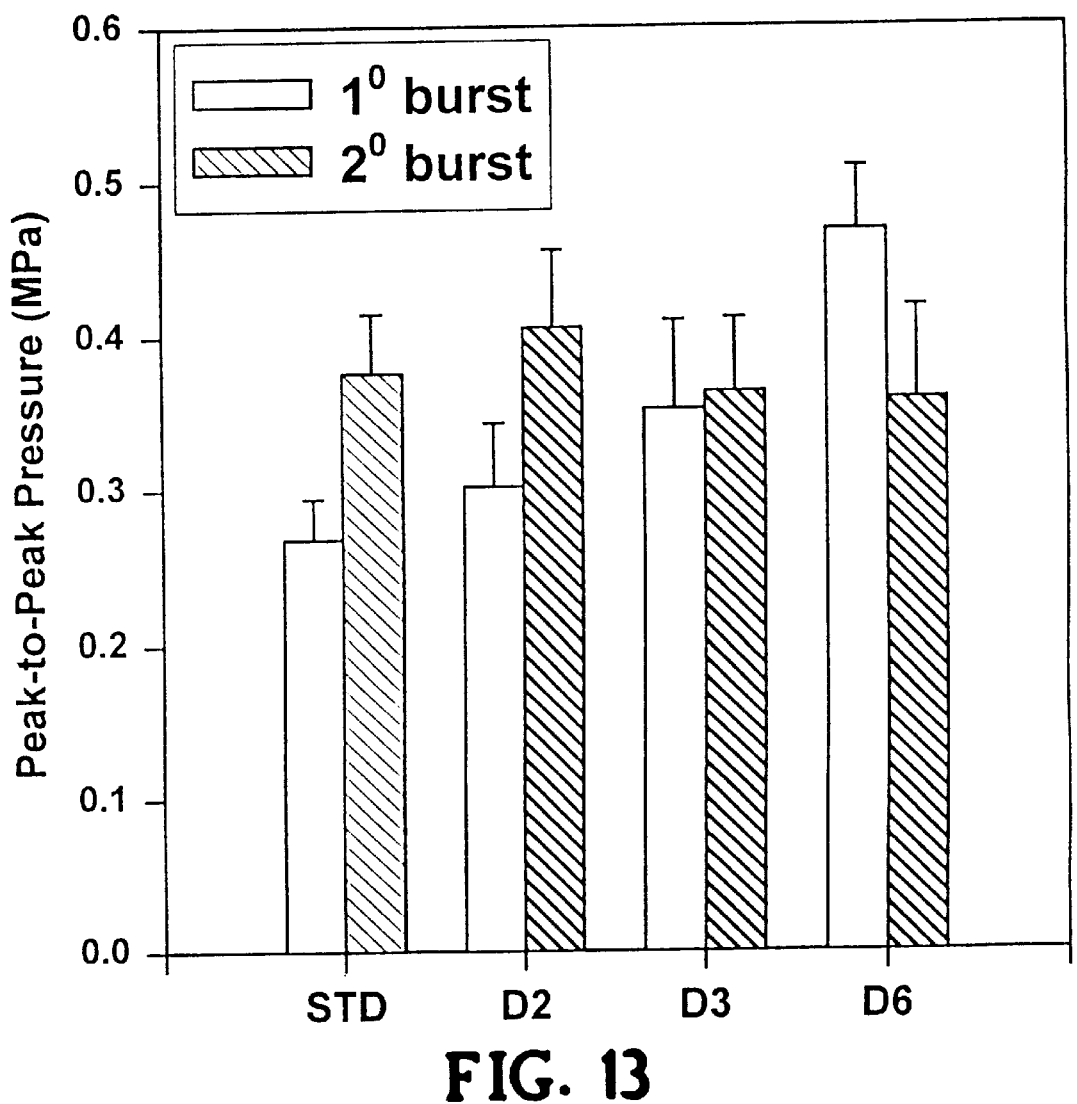
FIG. 13 is a graph showing the peak-to-peak amplitudes of the acoustical emission signals produced by a standard lithotripter at 25 kV, using the standard lithotripter reflector and the different ring reflector configurations of the present invention.
Figure 14:
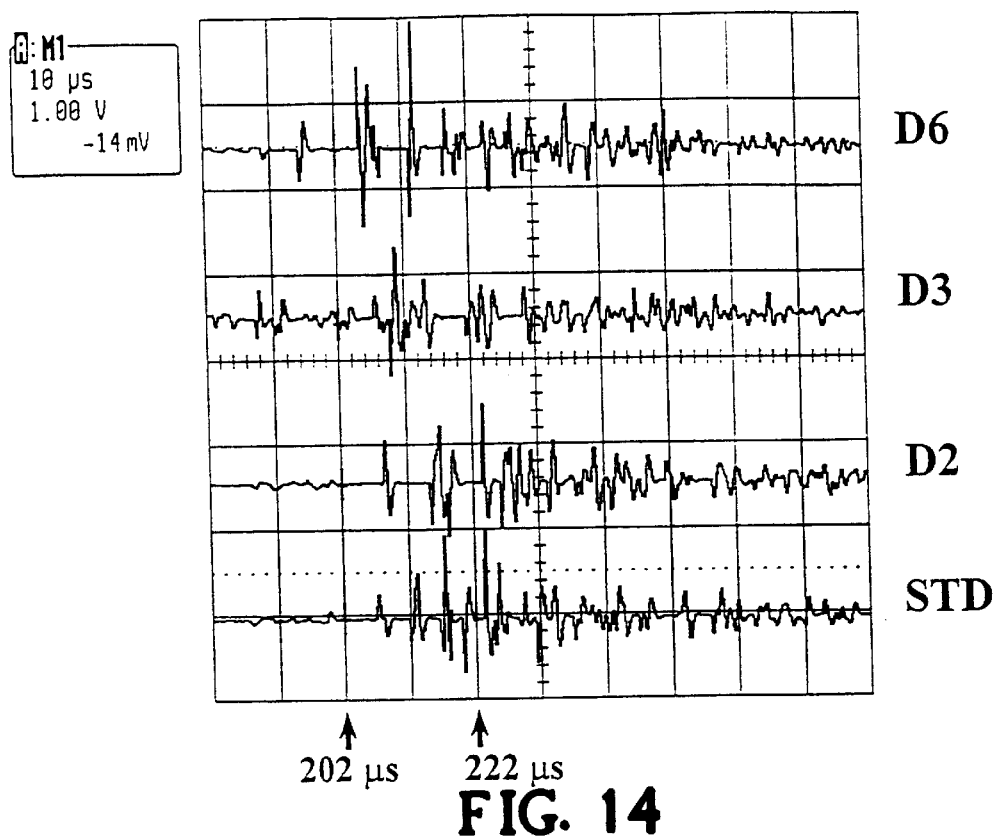
FIG. 14 is a graph showing the expansion of the initial portion of the acoustic emission signals produced by different ring reflector configurations at 25 kV. A 20-$\mu$s window (from 202 to 222 $\mu$s) corresponds to the lithotripter shock wave moving from 15 mm in front of F2 to 15 mm beyond F2.
Figure 15:
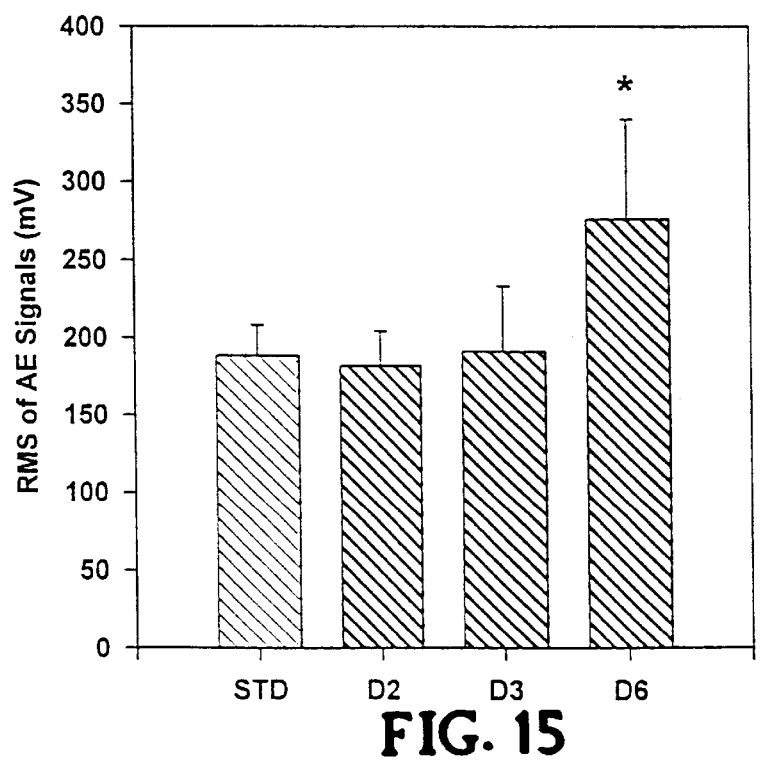
FIG. 15 is a graph showing the RMS of the acoustic emission signals in the 20-$\mu$s window shown in FIG. 14 to illustrate that the peak-to-peak amplitude produced by the D6 reflector configuration is significantly higher ($p<0.04$) than that from the standard reflector.

Similar characteristics of shock wave propagation and in situ microbubble-shock wave interaction were also observed inside the pipette used for the bioeffects study. Pipette 84 (See FIG. 3) was filled with saline solution and a yellow filter was used to reduce the light intensity in the surrounding water so that a uniformly illuminated image could be recorded. Using the ring reflector 42 configurations of the present invention, inertial microbubbles were induced in front of the lithotripter shock wave (LSW) and a more uniformly distributed bubble cluster was produced inside the pipette 84, compared to the original reflector 40. In the later stage (>200 $\mu$s), larger bubbles were formed both on the interior and exterior surface of the pipette 84 wall. These large bubbles lasted longer than the bubble cluster formed inside the pipette 84. Therefore, no clear observation of the bubble expansion and collapse inside the pipette 84 could be obtained.

c. Acoustic emission (AE): Using both the standard and ring reflector configurations of the present invention, AE signals with at least two distinct, temporally separated pressure bursts were recorded as shown in FIG. 11. The first pressure burst (1°) corresponds to the initial compression and subsequent expansion of cavitation nuclei by the incident shock wave, and the second burst (2°) to the primary collapse of the bubble cluster. In water, a third pressure burst (3°) was often recorded which was found to correlate with the collapse of aggregated large bubbles near F2. Using ring reflector (D6), the peak pressure of the first AE burst was found to be much stronger than that produced by the original reflector 40. This is primarily caused by the in situ shock wave-inertial microbubble interaction, with resultant violent collapse of microbubbles and strong secondary shock wave emission. The scattering of the incident lithotripter shock wave (LSW) from the microbubbles may also attribute to the increased peak pressure in the first AE burst. In addition, the collapse time of the bubble cluster ($t_c$) as illustrated in FIG. 12, defined as the time delay between the maximum pressure peaks of the first and second AE bursts, was found to increase from original reflector to stayed double reflector 40 of the present invention in accord with the strength of the preceding shock wave. In FIG. 13, a similar increase in the peak-to-peak amplitude of the first AE burst was also observed. However, the peak-to-peak pressure of the second AE burst was almost independent of the ring reflector 42 configuration (D2, D3, D6), since it is determined primarily by the inertial collapse of the expanded bubbles. When acoustic barrier materials were used to mask the lithotripter shock wave (LSW), the collapse time of the microbubbles induced by the preceding shock waves was determined to be between 9 to 17 $\mu$s. This result suggests that some microbubbles may be collapsed by the lithotripter shock wave near their maximum size while others may be collapsed after their maximum expansion. Furthermore, as illustrated by FIG. 14, a close examination of the initial portion of the first AE burst revealed some subtle differences between bubble activity produced by the original reflector 40 and ring reflector 42. In a 20-$\mu$s time window (from 202 to 222 $\mu$s, corresponding to the lithotripter shock wave moving from 15 mm in front of F2 to 15 mm beyond F2), the averaged amplitude (RMS) of the AE signal produced by the D6 ring reflector 42 configuration was found to be significantly stronger than that by the original reflector 40 as illustrated by FIG. 15. This result confirms again that in situ shock wave-microbubble interaction produces strong bubble collapse and secondary shock wave emission.

2. Bioeffects Study

To assess the bioeffects of the modified shock waves, shock wave mediated dextran transfer to a line of T-cell hybridoma that resembles activated T lymphocytes was tested. These hybridoma cells possess morphological and physiological features typical of most hematopoietic progenitor cells. In addition, the uniform cellular and nuclear morphology of the cell line allows easy detection of cellular damage and necrosis by DIC microscopy. Necrosis is also detected by trypan blue assay. Dextrans were chosen to characterize the efficiency of shock wave-induced membrane permeabilization because they are spherical molecules that are non-charged yet highly hydrophilic. These molecules, with an average molecular weight of 70 kD, mimics many proteins and hydrophilic macromolecules in their biophysical properties. The fluorescently conjugated dextran molecules also allow quick detection of the delivery, minimizng errors in quantification due to exocytosis.

Figure 16:
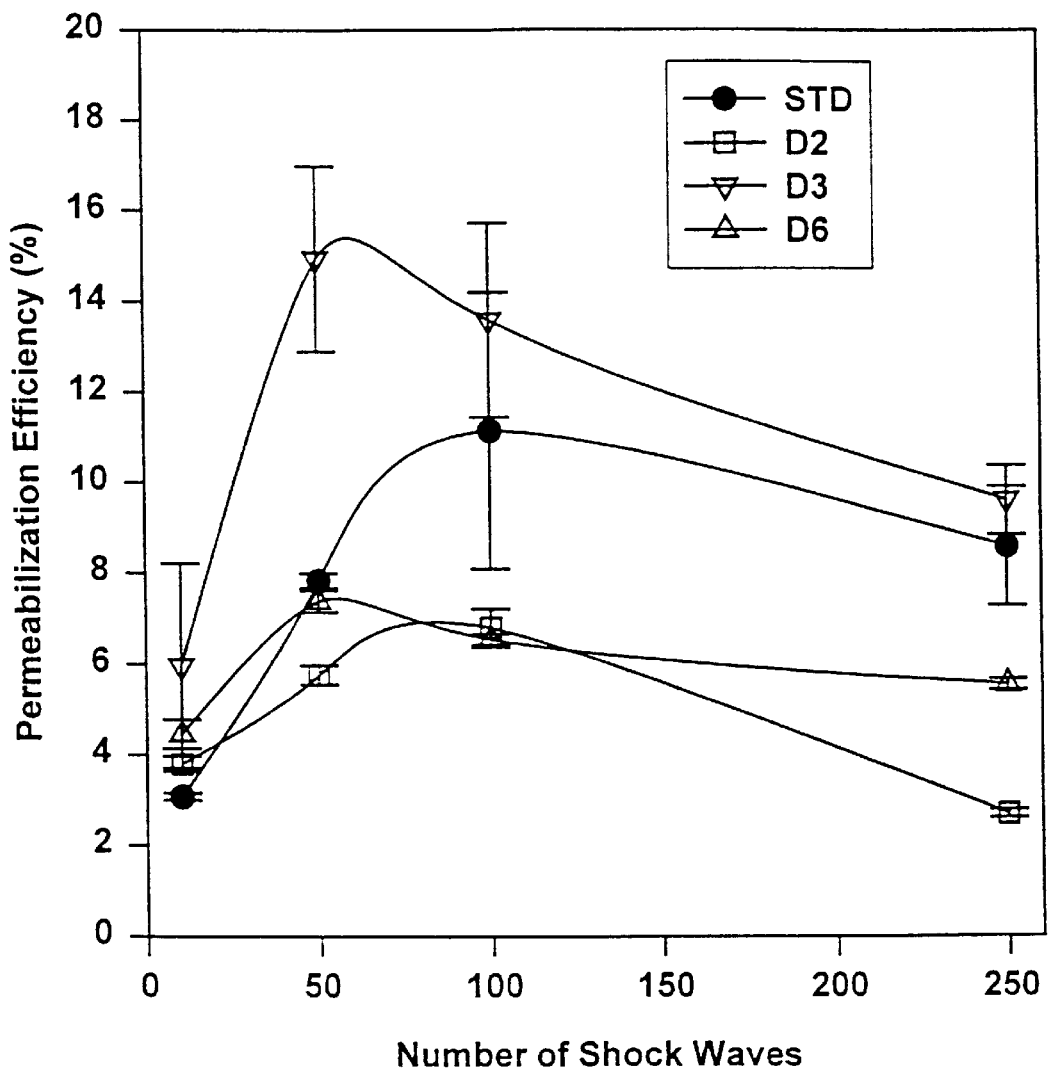
FIG. 16 is a graph showing the dose-dependent permeabilization efficiency of mouse T-cell hybridoma at 25 kV to illustrate that the permeabilization efficiency produced by the D3 reflector configuration of the present invention at 50 shocks is significantly higher ($p<0.03$) than that from the standard lithotripter reflector.
Figure 17:
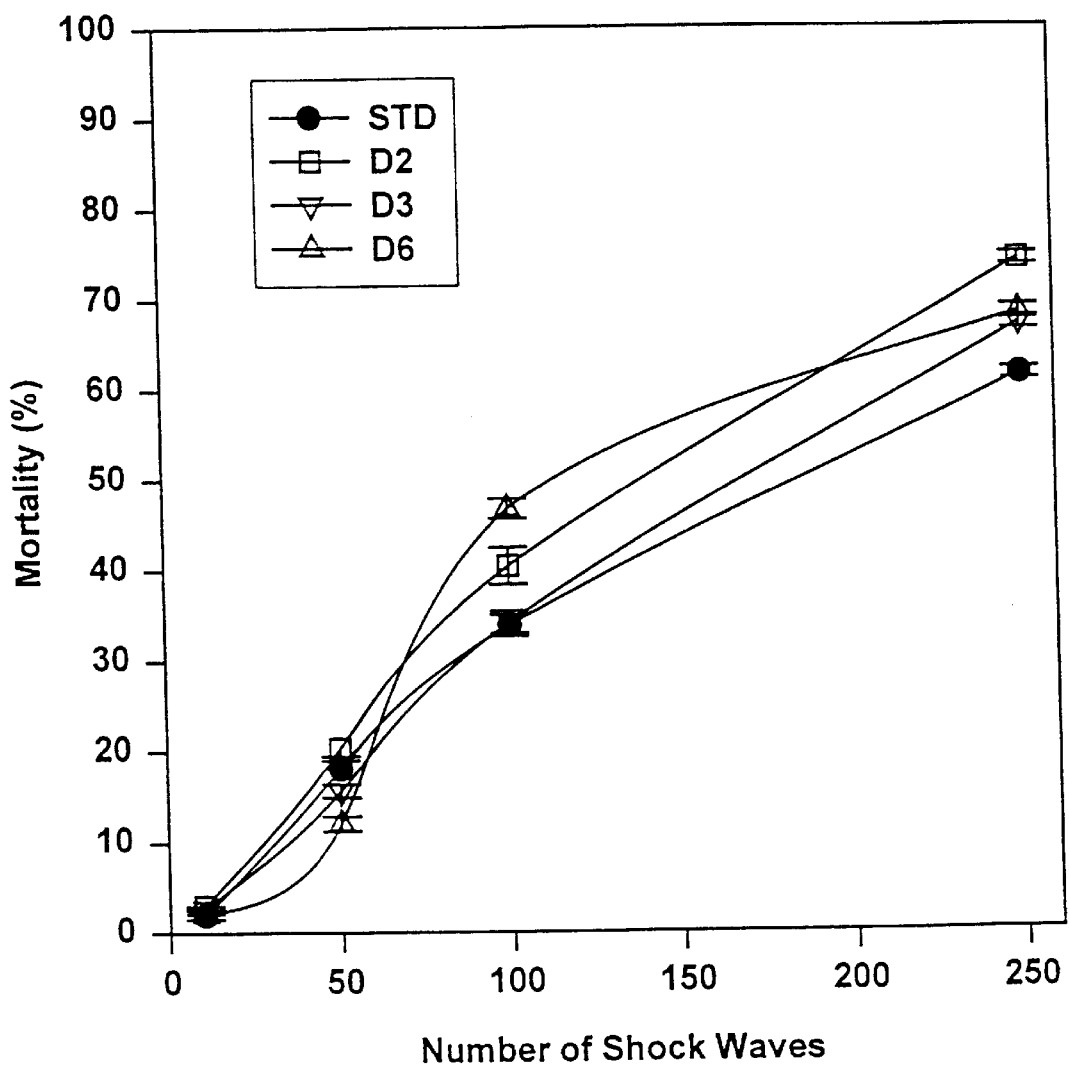
FIG. 17 is a graph showing dose-dependent cell mortality of mouse T-cell hybridoma at 25 kV to illustrate that the maximum cell mortality produced by the shock waves corresponding to the different ring reflector configurations of the present invention is significantly higher ($p<0.004$) than that from the standard lithotripter reflector.
Figure 18:
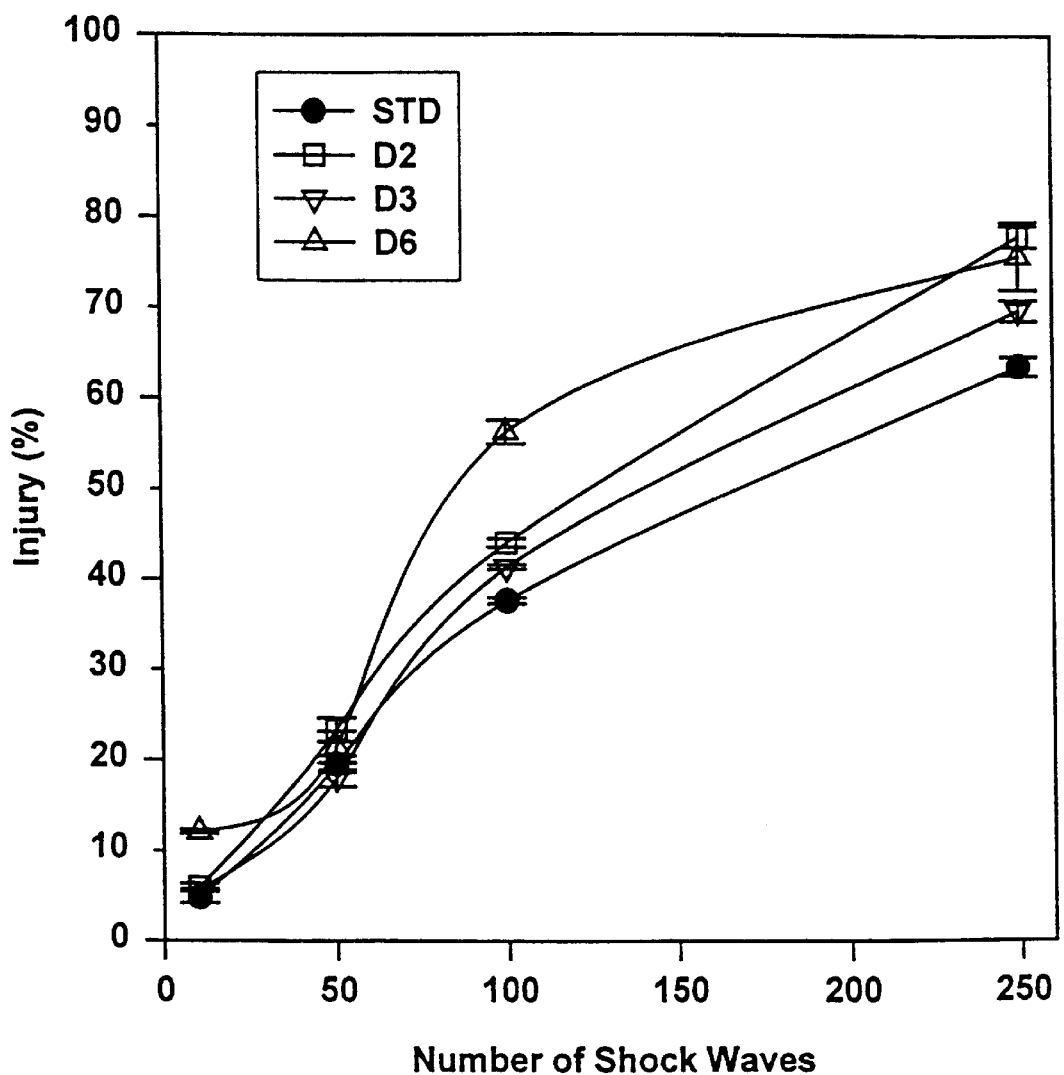
FIG. 18 is a graph showing dose-dependent cell injury of mouse T-cell hybridoma at 25 kV to illustrate that the maximum cell injury produced by the shock waves corresponding to the different ring reflector configuration of the present invention is significantly higher ($p<0.02$) than that from the standard lithotripter reflector.

As illustrated in FIGS. 16, 17, and 18, there is a clear dose-dependent response in cell membrane permeabilization efficiency, cell mortality and injury after shock wave treatment at 25 kV. Referring to FIG. 16, using lithotripter shock waves, permeabilization efficiency was found to increase initially with number of shock waves delivered to the target cells, and reach a maximum value at 100 shocks. In comparison, using the staged double reflector 38 of the present invention, the maximum permeabilization efficiency was achieved between 50 to 100 shocks. Interestingly, the permeabilization efficiency produced by the D3 ring reflector 42 configuration was found to be consistently higher than that produced by the original reflector 40 alone, while corresponding values from the D2 and D6 reflector 42 configurations were lower. This result suggests that there is an optimal combination of the preceding and lithotripter shock waves that can produce the best permeabilization efficiency, presumably related to the optimal shock wave-microbubble interaction.

Referring to FIG. 17, ring reflector 42 produces consistently higher cell death when the number of shock waves delivered exceeds 100 shocks, compared to when an original lithotripter reflector 40 is used alone. Similar results were also observed for cell injury as illustrated in FIG. 18, which only shifts slightly higher from the mortality curves. This result indicates that most cells were physically damaged, and a small percentage of survival cells were physiologically impaired.

In conclusion, the present invention is an apparatus and method to improve the efficiency of SWL-induced bioeffects, by producing reliable shock wave-inertial microbubble interaction via a ring reflector 42 connected to a standard ellipsoidal reflector 40 of electrohydraulic shock wave lithotripters. A weak shock wave, preceding the regular lithotripter pulse by a few microseconds, was generated by wave reflection and diffraction from a ring reflector 42 mounted on the rim of a lithotripter reflector 40. This preceding shock wave produces inertial microbubbles, which expand to a maximum size of 100~200 μm before being collapsed in situ by the lithotripter shock wave. Because of this interaction, strong secondary shock wave emission and microjet formation are produced immediately following the propagating lithotripter shock front. These characteristic features are absent from bubble dynamics induced by the standard lithotripter shock waves and thus likely causing the differences in the observed bioeffects. Compared to the standard lithotripter pulses, injury of mouse T-cell hybrodoma exposed to the shock waves reflected by the staged double reflector 38 of the invention was found to be consistently higher at high dosage (6%~50%, pulse number >100). In addition, combined with appropriate preceding shock waves of the invention, the efficiency of cell membrane permeabilization by lithotripter shock waves at low dosage (50~100 shocks) can be enhanced significantly in the range of 34% to 91%. These findings demonstrate clearly that shock wave-inertial microbubble interaction can be used to improve the bioeffects of lithotripter shock waves.

The interaction of a lithotripter shock wave with an artificially produced stable air bubble has been studied previously. It was shown that corresponding to the temporal profile of the shock wave, bubbles within certain size range would be collapsed asymmetrically, leading to the formation of microjets along the wave propagation direction. For a typical XL-1 lithotripter shock wave, this initial size (diameter) range is between 0.5 to 1.5 mm, with maximum jet velocity obtained at about 1.0 mm. When the size of the stable bubble decreases, the momentum transfer during shock wave-bubble interaction also decreases, resulting in a lower potential for asymmetric collapse of the bubble. Using the XL-1 lithotripter, it was shown that as the bubble diameter becomes less than 500 μm, microjets would not be produced consistently. Furthermore, the internal pressure of a stable bubble increases rapidly when compressed by a lithotripter shock wave front (assuming adiabatic gas compression inside the bubble), leading to a cushion effect against the violent collapse of the bubble.

In comparison, using the ring reflectors 42 of the present invention, inertial microbubbles are produced acoustically and expanded to more than 4600~37000 times (corresponding to $R_{bmax}$=100~200 μm and assuming initial cavitation nuclei are 6 μm in diameter) in volume before being collapsed in situ by the ensuring lithotripter shock wave. Because of this large expansion, the internal pressure of the inertial microbubble when impinged by a lithotripter shock wave is much lower compared to a stable bubble of the same size. Therefore, the cushion resistance against the collapse of inertial microbubbles is very low. This explains why violent collapse of the inertial microbubbles and microjet formation were produced consistently using the ring reflector 42 of the present invention, as revealed by high-speed shadowgraphy. In addition, based on the results of AE measurements, it is interesting to note that the forced collapse of inertial microbubbles is as strong as or even stronger than the inertial collapse of large bubbles. Considering that the bubble expansion produced by current lithotripter shock waves in vivo could be severely constrained by surrounding tissue and may cause capillary and small blood vessel rupture, shock wave-inertial microbubble interaction is an attractive alternative for shock wave-mediated drug delivery and gene transfer in vivo, with less potential for vascular injury.

Forced collapse of inertial cavitation bubbles can also be produced by phase-inverted lithotripter shock waves. Several groups have used pressure-released reflectors to invert the typical lithotripter shock waves to produce a pressure waveform with a leading tensile component followed by a compressive wave. With such a phase-inverted lithotripter shock wave, in situ shock wave-inertial bubble interaction can also be produced. However, because there is no time delay between the leading tensile wave (which is quite strong) and the following shock front, the shock wave-bubble interaction occurs during the initial rapid expansion phase of the bubbles. Consequently, a significant portion of the shock wave energy is consumed to terminate the rapid expansion of the bubbles, and thus less shock wave energy is used for the collapse of the bubbles. In addition, the phase-inverted lithotripter shock waves are less flexible in terms of controlling the area of shock wave-bubble interaction, as well as the pressure and energy ratio between the leading tensile wave and the following compressive wave, since both of them are generated by the same reflector surface. In comparison, using a ring reflector 42 of the present invention, a preceding weak shock wave with a tensile stress sufficiently strong enough to induce inertial microbubbles can be produced. The strength and the time delay between the preceding pulse and lithotripter shock wave can be adjusted so that the inertial microbubbles are collapsed near their maximum size. Thus, most of the lithotripter shock wave energy consumed during the shock wave-inertial microbubble interaction is used for the collapse of the bubbles. Moreover, by adjusting the size and configuration of the ring reflector 42, we can also control the size and distribution of inertial microbubbles around the lithotripter focal point. This strategy may be used to control the area of shock wave-bubble interaction to achieve optimal therapeutic effects (i.e. drug delivery and gene transfer) to the target cells with minimal damage to surrounding tissues. Our results indicate that an appropriate combination between the preceding shock wave, which induces inertial microbubbles, and the ensuing shock wave, which collapses the microbubbles, is needed in order to achieve the best peameabilization efficiency.

On the other hand, the interaction of lithotripter shock waves with larger cavitation bubbles (>1 mm) may be more suitable for tissue destruction, utilizing the strong bubble expansion and subsequent violent collapse of the bubbles.

While the invention has been described in reference to specific embodiments thereof, it will be appreciated that numerous variations, modifications, and embodiments are possible, and accordingly, all such variations, modifications, and embodiments are to be regarded as being with in the spirit and scope of the invention.

What is claimed is:

1. An apparatus for non-invasive delivery of macromolecules into living cells comprising;
    a) means for generating first and second pulses, wherein said first pulse precedes said second pulse by a time period and is weaker than said second pulse; and b) means for applying said first and second pulses to said living cells causing transient membrane permeability thereof resulting in uptake of said macromolecules into said cells.

2. An apparatus according to claim 1, wherein said means for generating said first and second pulses comprises means for generating acoustic waves.

3. An apparatus according to claim 1, wherein said means for generating said first and second pulses comprises a lithotripter.

4. An apparatus according to claim 1, wherein said means for generating said first and second pulses comprises a localized explosive device.

5. An apparatus according to claim 1, wherein said means for generating said first and second pulses comprises a laser.

6. An apparatus according to claim 1, wherein said means for generating said first and second pulses comprises means for generating an initial pulse, and first and second reflectors, wherein said initial pulse is reflected partially from said first reflector as said first pulse and partially from said second reflector as said second pulse.

7. An apparatus according to claim 6, wherein the major axis of said first reflector is shorter than the major axis of said second reflector.

8. An apparatus according to claim 6, wherein said second reflector is a truncated ellipsoidal reflector and said first ellipsoidal reflector is integral therewith.

9. An apparatus according to claim 1, wherein said first pulse precedes said second pulse by approximately 2.0 to 19.0 $\mu$s.

10. An apparatus according to claim 1, wherein said first pulse has a low positive pressure compared to said second pulse.

11. An apparatus according to claim 1, wherein said first pulse has a peak positive pressure in the range of approximately +1 to +10 MPa.

12. An apparatus according to claim 1, wherein said first pulse has a peak negative pressure in the range of −5.0 to −0.5 MPa.

13. An apparatus according to claim 1, wherein said first pulse has a peak positive and peak negative pressure that may be varied in strength.

14. An apparatus according to claim 1, wherein said time period may be varied in length.

15. An apparatus according to claim 1, wherein said second pulse has a peak positive pressure of approximately +100 to +20 MPa.

16. An apparatus according to claim 1, wherein said second pulse has a negative pressure of approximately −17.0 to −1.0 MPa.

17. An apparatus according to claim 1, wherein said second pulse has a significantly reduced peak negative pressure such that said second pulse does not induce cavitation.

18. A lithotripter for non-invasive delivery of macromolecules into living cells comprising:
a) means for generating first and second pulses, wherein said first pulse precedes said second pulse by a time delay and is weaker than said second pulse;
b) means for applying said first and second pulses to said living cells causing transient membrane permeability thereof resulting in uptake of said macromolecules into said cells.

19. A lithotripter according to claim 18, wherein generating said first and second pulses comprises generating an initial pulse, and providing first and second reflectors, and reflecting said initial pulse partially from said first reflector as said first pulse and partially from said second reflector as said second pulse.

20. A lithotripter according to claim 19, wherein the major axis of said first reflector is shorter than the major axis of said second reflector.

21. A lithotripter according to claim 19, wherein said second reflector is a truncated ellipsoidal reflector and said first reflector is an annular ring reflector attached thereto.

22. A lithotripter according to claim 18, wherein said first pulse precedes said second pulse by approximately between 2.0 to 19.0 $\mu$s.

23. An apparatus according to claim 18, wherein said first pulse has a low positive pressure compared to said second pulse.

24. An apparatus according to claim 18, wherein said first pulse has a peak positive pressure in the range of approximately +1.0 to +10.0 MPa.

25. An apparatus according to claim 18, wherein said first pulse has a peak negative pressure in the range of approximately −5.0 to −0.5 MPa.

26. An apparatus according to claim 18, wherein said second pulse has a peak positive pressure of approximately +100 to +20 MPa.

27. An apparatus according to claim 18, wherein said second pulse has a peak negative pressure of approximately −17.0 to −1.0 MPa.

28. An apparatus according to claim 18, wherein said second pulse has a significantly reduced peak negative pressure such that said second pulse does not induce cavitation.

29. A method for delivery of macromolecules into living cells comprising the steps of:
a) providing macromolecules to an area surrounding said living cells;
b) generating a first pulse and a second pulse, wherein said first pulse precedes said second pulse by a time period and is weaker than said second pulse; and
c) applying said first and second pulse to said living cells, thereby causing transient membrane permeability thereof resulting in uptake of said macromolecules into said living cells.

30. The method according to claim 29, comprising said first pulse expanding cavitational nuclei adjacent said living cells to form inertial microbubbles.

31. The method according to claim 30, comprising said second pulse imploding said inertial microbubbles, thereby forming secondary shock waves and microjets resulting in transient membrane permeability of said living cells.

32. The method according to claim 30, comprising collapsing inertial microbubbles when at near their maximum size.

33. The method according to claim 30, comprising adjusting the strength of said first pulse and said time period between said first and second pulses such that said inertial microbubbles are collapsed approximately their maximum size.

34. The method according to claim 30, comprising adjusting the strength of said pulse and said time delay between said first and second pulses to control the size and distribution of said inertial microbubbles around said living cells.

35. An method according to claim 30, comprising reducing the peak negative pressure such that said second pulse does not induce cavitation.

36. The method according to claim 29, wherein the macromolecule is in a solution surrounding said living cells in vitro.

37. The method according to claim 29, wherein said providing comprises administering said macromolecules to the living cells of a patient prior to said applying said first and second pulses to said living cells in vivo.

38. The method according to claim 37, wherein said patient is human.

39. The method according to claim 37, wherein said patient is a mammal.

40. The method according to claim 38, wherein said patient has a genetic disease.

41. The method according to claim 38, wherein said patient has a non-genetic disease.

42. The method according to claim 29, wherein said macromolecule is a drug.

43. The method according to claim 29, wherein said living cells are diseased cells.

44. The method according to claim 29, wherein the macromolecule comprises a nucleic acid, protein, or other hydrophilic macromolecules.

45. The method according to claim 44, wherein said nucleic acid comprises DNA.

46. The method according to claim 45, wherein said DNA comprises a gene.

* * * * *

UNITED STATES PATENT AND TRADEMARK OFFICE
CERTIFICATE OF CORRECTION

PATENT NO.   : 6,298,264 B1
DATED        : October 2, 2001
INVENTOR(S)  : Pei Zhong, Franklin H. Cocks, Glenn M. Preminger and Haifan Lin It is certified that error appears in the above-identified patent and that said Letters Patent is hereby corrected as shown below:

<u>Column 1</u>,
Delete lines 5-9.

Signed and Sealed this

Twenty-fifth Day of June, 2002

Attest:

JAMES E. ROGAN
*Attesting Officer*   *Director of the United States Patent and Trademark Office*